US00PP16100P2

(12) United States Plant Patent
Kratzenberg

(10) Patent No.: US PP16,100 P2
(45) Date of Patent: Nov. 8, 2005

(54) *CAMPANULA* PLANT NAMED 'BENCAMP 46'

(50) Latin Name: ***Campanula cochleariifolia*×*Campanula fragilis***
Varietal Denomination: Bencamp 46

(75) Inventor: Sabine Kratzenberg, Muenden (DE)

(73) Assignee: Ernst Benary Samenzucht GmbH, Muenden (DE)

( * ) Notice: Subject to any disclaimer, the term of this patent is extended or adjusted under 35 U.S.C. 154(b) by 22 days.

(21) Appl. No.: 10/923,984

(22) Filed: Aug. 23, 2004

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM, Plant Variety Database, 2004/06, GTI Jouve Retrieval Software, Citation for Campanula 'Bencamp 46'.*

* cited by examiner

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Campanula* plant named 'Bencamp 46', characterized by its upright and outwardly spreading growth habit; small violet-colored flowers; long flowering period; and good garden performance.

1 Drawing Sheet

Botanical classification/cultivar designation: *Campanula cochleariifolia*×*Campanula fragilis* cultivar Bencamp 46.

BACKGROUND OF THE INVENTION

The present Invention relates to a new and distinct cultivar of *Campanula* plant, botanically known as *Campanula cochleariifolia*×*Campanula fragilis* and hereinafter referred to by the name 'Bencamp 46'.

The new *Campanula* is a product of a planned breeding program conducted by the Inventor in Gimte, Germany. The objective of the breeding program is to create new freely-flowering interspecific *Campanula* cultivars.

The new *Campanula* originated from a cross-pollination made by the Inventor in 1993 of an unnamed selection of *Campanula cochleariifolia*, not patented, as the female, or seed parent, with an unnamed selection of *Campanula fragilis*, not patented, as the male, or pollen parent. The new *Campanula* was discovered and selected as a single flowering plant from the resulting progeny of the stated cross-pollination by the Inventor in a controlled environment in Gimte, Germany in 1994.

Asexual reproduction of the new cultivar by cuttings in Gimte, Germany since 1994, has shown that the unique features of this new *Campanula* are stable and reproduced true to type in successive generations.

SUMMARY OF THE INVENTION

Plants of the cultivar Bencamp 46 have not been observed under all possible environmental conditions. The phenotype may vary somewhat with variations in environment such as temperature and/or light intensity without, however, any variance in genotype.

The following traits have been repeatedly observed and are determined to be the unique characteristics of 'Bencamp 46'. These characteristics in combination distinguish 'Bencamp 46' as a new and distinct cultivar:

1. Upright and outwardly spreading growth habit.
2. Small violet-colored flowers.
3. Long flowering period.
4. Good garden performance.

Plants of the new *Campanula* can be compared to plants of the female parent selection. Plants of the new *Campanula* differ from plants of the female parent selection in the following characteristics:

1. Plants of the new *Campanula* are more upright than plants of the female parent selection.
2. Flowers of plants of the new *Campanula* are more open than flowers of plants of the female parent selection.
3. Plants of the new *Campanula* have shorter peduncles than plants of the female parent selection.

Plants of the new *Campanula* can be compared to plants of the male parent selection. Plants of the new *Campanula* differ from plants of the male parent selection in the following characteristics:

1. Plants of the new *Campanula* are more outwardly spreading than plants of the male parent selection.
2. Flowers of plants of the new *Campanula* are larger than flowers of plants of the male parent selection.
3. Plants of the new *Campanula* have better garden performance than plants of the male parent selection.

Plants of the new *Campanula* can be compared to plants of the *Campanula* cultivar Clips, not patented. In side-by-side comparisons conducted in Gimte, Germany, plants of the new *Campanula* differed from plants of the cultivar Clips in the following characteristics:

1. Plants of the new *Campanula* were more outwardly spreading than plants of the cultivar Clips.
2. Flowers of plants of the new *Campanula* were smaller than flowers of plants of the cultivar Clips.
3. Plants of the new *Campanula* flowered for a longer period of time than plants of the cultivar Clips.
4. Plants of the new *Campanula* had better garden performance than plants of the cultivar Clips.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new *Campanula.*

The photograph at the bottom of the sheet comprises a side perspective view of typical plants of 'Bencamp 46'.

The photograph at the top of the sheet comprises a close-up view of typical flowers and leaves of 'Bencamp 46'.

DETAILED BOTANICAL DESCRIPTION

In the following description, color references are made to The Royal Horticultural Society Colour Chart, 1995 Edition, except where general terms of ordinary dictionary signigicance are used. Plants used for the above-mentioned photographs and botanical description were grown in Bonsall, Calif. during the late spring with three plants per 20-cm containers in a polyethylene-covered greenhouse. During the production of the plants, day temperatures ranged from 10 to 21° C. and night temperatures ranged from 4 to 10° C. Plants used were about 16 weeks old when the photographs and description were taken.

Botanical classification: *Campanula cochleariifolia*× *Campanula fragilis* cultivar Bencamp 46.

Parentage:

*Female, or seed, parent.*—Unnamed selection of *Campanula cochleariifolia,* not patented.

*Male, or pollen, parent.*—Unnamed selection of *Campanula fragilis,* not patented.

Propagation:

*Type.*—By cuttings.

*Time to initiate roots.*—About two weeks at 18° C.

*Root description.*—Fibrous, fine; white in color.

Plant description:

*Form.*—Upright and outwardly spreading; inverted triangle.

*Plant height, soil level to top of plant plane.*—About 12 cm.

*Plant width, single plant.*—About 18 cm.

*Lateral branch description.*—Quantity: About eight to ten per plant. Length: About 22 cm. Diameter: About 2.5 mm. Internode length: About 6 to 15 mm. Texture: Smooth, glabrous. Color, immature: 144A. Color, mature: 182B.

*Foliage description.*—Arrangement: Alternate, simple. Length: About 2 cm. Width: About 2.3 cm. Shape: Rounded deltoid. Apex: Rounded. Base: Slightly cordate. Margin: Crenate. Texture, upper and lower surfaces: Smooth, glabrous. Venation pattern: Pinnate. Color: Developing foliage, upper and lower surfaces: 146A. Fully expanded foliage, upper surface: 147A. Fully expanded foliage, lower surface: 147B. Venation, upper and lower surfaces: 146B. Petiole: Length: About 3.8 mm. Diameter: About 2 mm. Texture, upper and lower surfaces: Smooth; glabrous. Color, upper and lower surfaces: 146B.

Flower description:

*Flower type and habit.*—Small, single, axillary and campanulate flowers. Flowers face mostly upright and outward. Flowers persistent. Flowers not fragrant.

*Natural flowering season.*—Long flowering period; March through May in Southern California.

*Quantity.*—Freely flowering with about two to three flowers and about four flower buds per lateral branch.

*Flower longevity on the plant.*—About one week.

*Flower diameter.*—About 2.7 cm.

*Flower depth (height).*—About 1.8 cm.

*Flower buds.*—Length: About 1.5 cm. Diameter: About 6 mm. Shape: Oblong. Color: 92B.

*Petals.*—Quantity per flower: Five in a single whorl; fused towards the base. Length: About 8 mm. Width: About 8 mm. Shape: Deltoid. Apex: Acute. Margin: Entire. Texture, upper and lower surfaces: Smooth; glabrous; velvety. Color: When opening, upper surface: 92A. When opening, lower surface: 92B. Fully opened, upper surface: Towards the apex, slightly more blue than 85A; mid-section, 85B; towards the base, 85C. Fully opened, lower surface: 85A.

*Sepals.*—Quantity per flower: Five in a single whorl; fused towards the base. Length: About 8 mm. Diameter: About 2 mm. Shape: Linear. Apex: Acute. Margin: Entire. Texture, upper and lower surfaces: Smooth, glabrous. Color, upper and lower surfaces: 146A.

*Peduncles.*—Length: About 3 cm. Diameter: About 1 mm. Angle: About 15° from vertical. Strength: Strong. Texture: Smooth, glabrous. Color: 146B.

*Reproductive organs.*—Androecium: Stamens per flower: Five. Anther shape: Linear. Anther size: About 1 mm by 5 mm. Anther color: 10C. Pollen amount: Scarce. Pollen color: 10D. Gynoecium: Pistils per flowers: One. Pistil length: About 1.7 cm. Style length: About 1.1 cm. Style color: 92A to 92B. Stigma shape: Tri-parted; recurved. Stigma color: 10D. Ovary color: 1C.

*Seeds/fruit.*—Seed and fruit production have not been observed.

Disease/pest resistance: Under commercial production conditions, plants of the new *Campanula* have not been noted to be resistant to pathogens or pests common to *Campanula.*

Garden performance: Plants of the new *Campanula* have been observed to have good garden performance and tolerate rain, wind and temperatures from −15 to 38° C.

It is claimed:

1. A new and distinct cultivar of *Campanula* plant named 'Bencamp 46', as illustrated and described.

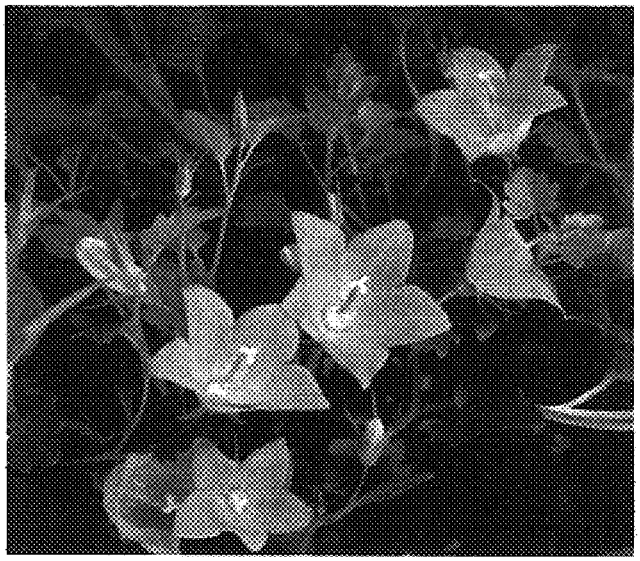
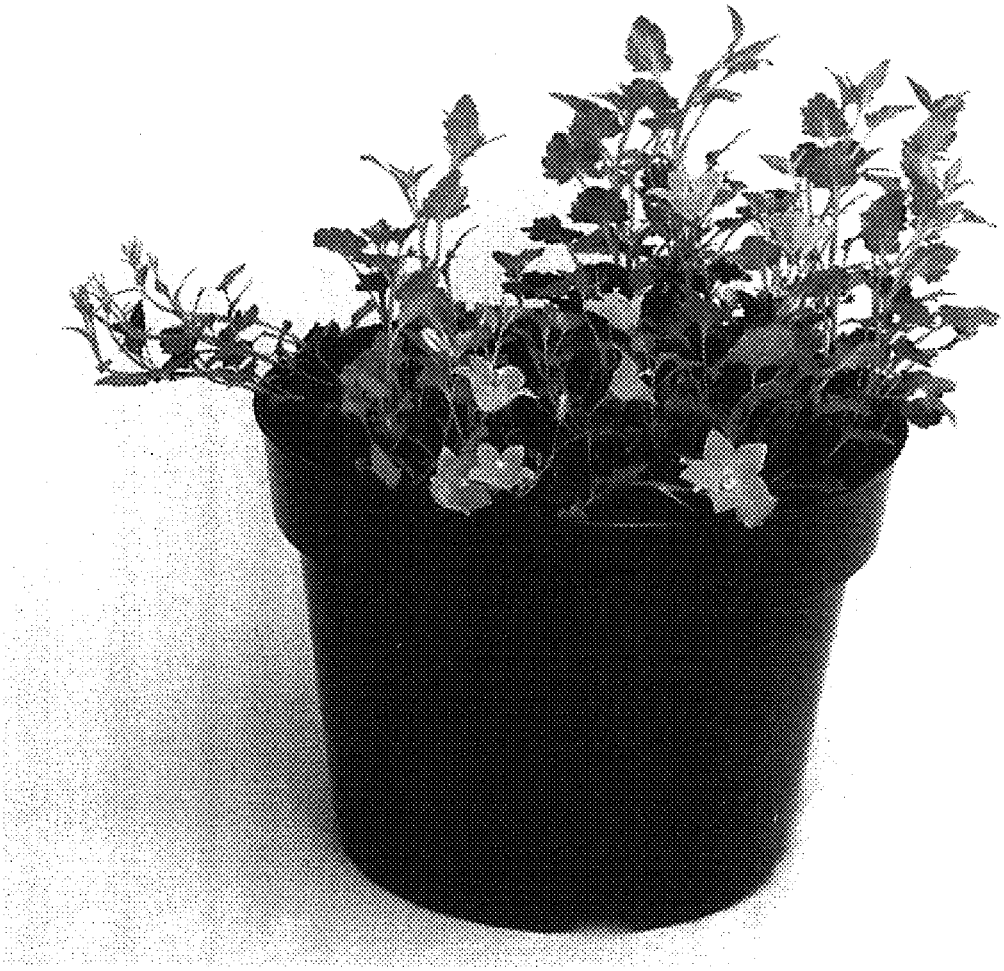

* * * * *